United States Patent [19]

Lin et al.

[11] Patent Number: 4,481,370

[45] Date of Patent: Nov. 6, 1984

[54] METHOD FOR THE PREPARATION OF BENZENAMINES

[75] Inventors: Henry C. Lin; Byron R. Cotter, both of Grand Island, N.Y.

[73] Assignee: Occidental Chemical Corporation, Niagara Falls, N.Y.

[21] Appl. No.: 504,637

[22] Filed: Jun. 15, 1983

[51] Int. Cl.$^3$ ............................................. C07C 85/00
[52] U.S. Cl. ................................................... 564/394
[58] Field of Search ........................................ 564/394

[56] References Cited

U.S. PATENT DOCUMENTS 3,832,364  8/1974  Coulson ........................ 564/394 X

*Primary Examiner*—Paul F. Shaver
*Attorney, Agent, or Firm*—James F. Tao; Arthur S. Cookfair

[57] ABSTRACT

A method for the preparation of aromatic amines comprises reacting hydrogen fluoride with a phenyl carbamic fluoride.

29 Claims, No Drawings

METHOD FOR THE PREPARATION OF BENZENAMINES

BACKGROUND OF THE INVENTION AND MATERIAL INFORMATION DISCLOSURE STATEMENT

This invention relates to a method for the preparation of aromatic amines.

The benzenamines, also known as anilines and as aminobenzenes, are a known class of compounds having commercial utility as chemical intermediates, for a wide range of chemical end products. Substituted benzenamines, especially trifluoromethyl-substituted benzenamines are particularly useful as intermediates for the preparation of various dyestuff and pesticides. For example, 2-Amino-5-chlorobenzotrifluoride (also known as 4-chloro-2-(trifluoromethyl)benzenamine), is employed commercially as a dye intermediate and is designated as C. I. Azoic Diazo Component 17, according to Colour Index, Chemical No. 37055, Vol. 1–4, 2nd ed. 1956, Suppl. 1963 published by the Society of Dyers and Colourists (U.K.) and The American Association of Textile Chemists and Colorists (U.S.).

Substituted benzenamines, such as (trifluoromethyl)-benzenamines are disclosed in U.S. Pat. No. 4,243,819 to Henrick et al., as intermediates in the synthesis of amino acid esters having pesticidal properties. Thus, for example, the reference teaches the preparation of such esters by reaction of various trifluoromethylanilines with m-phenoxybenzyl α-bromoisovalerate.

U.S. Pat. No. 4,316,988 to Clinton discloses the use of trifluoromethyl-substituted anilines as intermediates in the synthesis of various diphenylamine products useful as rodenticides, insecticides, and arachnicides.

The utility of benzenamines, including o-aminobenzotrifluorides as chemical intermediates has led to the investigation and development of various methods for the preparation of these compounds.

One known method for the preparation of aromatic amines, such as aniline, involves the reduction of an aromatic nitro compound. Thus, aniline may be prepared by reaction of nitrobenzene with hydrogen. McBee et al., J. Am. Chem. Soc. 73, 3932–34 (1951) disclose the preparation of 4-bromo-2-(trifluoromethyl)-aniline by nitration of 3-bromo-(trifluoromethyl)-benzene followed by reduction of the resultant 2-nitro-5-bromo(trifluoromethyl)-benzene.

U.S. Pat. No. 4,096,185 to Seiwell discloses the preparation of p-aminobenzotrifluoride (also known as 4-(trifluoromethyl)benzenamine) by reaction of p-chlorobenzotrifluoride with ammonia in a non-queous solvent in the presence of copper compound, such as cuprous chloride and a selected salt, such as potassium fluoride.

Forbes et al., Tetrahedron, Vol. 8, 67–72 (1960) prepared o-aminobenzotrifluoride by hydrogenation of 2-nitrotrifluoromethylbenzene at elevated temperatures and pressure in the presence of a Raney nickel catalyst.

German Offenlegungschrift D.E. No. 3,017,542 to Klauke et al. discloses the preparation of o-aminobenzotrifluoride by hydrogenation-hydrogenolysis of 2-amino-5-chlorobenzotrifluoride.

It is also known that isocyanates and carbamic acid fluorides are susceptible to hydrolysis, in a known manner, to form an amine. See Fieser and Fieser, *Organic Chemistry*, 3rd Ed D. C. Heath and Co. (1956). However, when the reaction is run neat, substantial quantities of urea may be formed as by-product. The formation of urea may be minimized, or avoided when a solvent, such as toluene, is employed, but the yields of amine are low.

Although methods for the preparation of aromatic amines, such as aminobenzotrifluorides are known from the prior art, it will be appreciated that the development of improved and more economical processes is desireable.

The present process differs substantially from the prior art process in the use of hydrogen fluoride and phenyl carbamic acid fluoride as reactants. The preparation of the phenyl carbamyl fluorides by reaction of phenyl isocyanates and hydrogen fluoride is known. Buckley et al. J. Chem. Soc. 864 (1945) disclose the preparation of phenyl carbamic acid fluorides by reaction of HF with various isocyanates. However, the reference provides no teaching relative to the fluorination of aromatic isocyanates bearing a haloalkyl side chain and no teaching or suggestion of the preparation of aromatic amines. The reference further discloses the treatment of phenylcarbamyl fluoride with water to result in the formation of diphenylurea.

British Pat. No. 955,898 (1964) to Farbenfabriken Bayer Aktiengesellschaft discloses the reaction of anhydrous hydrogen fluoride with chloromethylphenyl isocyanates to produce the corresponding fluoromethylphenyl carbamic acid fluoride, or, upon subsequent heating, the corresponding isocyanate. The British patent further discloses the reaction of hydrogen fluoride with 2-trichloromethyl-4-chlorophenyl isocyanate in chlorobenzene to prepare 2-trifluoromethyl-4-chlorophenyl carbamic acid fluoride. Subsequently, Klauke, Angew. Chem. Interat. Ed. Vol. 5, No. 9, 848, (1966), in contrast to the teachings of Brit. Pat. 955,898, stated that when o-trichloromethylphenyl isocyanate undergoes chlorine-fluorine exchange in anhydrous hydrogen fluoride; isomerization occurs simultaneously and o-N-(trifluoromethyl)aminobenzoyl fluoride can be isolated. In U.S. Pat. No. 3,829,460 to Buttner and Klauke assigned to Bayer Aktiengesellschaft, reference is made to the 1966 article and to earlier contradictory teachings and it is disclosed that when hydrogen fluoride is reacted with a trichloromethylphenyl isocyanate wherein the trichloromethyl group is in the 2-position to the isocyanate group, it is only possible to obtain the isomers, 2-N-trifluoromethylamino-benzoyl fluorides.

British Pat. No. 1,164,223 to Klauke et al. teaches the hydrolysis of trifluoromethylphenyl isocyanates with 90–100 percent sulfuric acid to produce the corresponding trifluoromethyl benzenamine (or amine.sulfate) with carbon dioxide as the only byproduct.

The hydrolysis of an NCO group with acid agent, such as concentrated hydrochloric acid or sulphamic acid is known (Houben-Weyl, Methoden der org. Chemie, 4th Edition, Vol. 11/1, page 953).

Although the utility and commercial value of aromatic amines has been generally recognized for many years; and, various investigations have been made of reactions of aromatic isocyanates, including aromatic isocyanates having a perchlorinated alkyl side chain, there has been no suggestion heretofore that aromatic amines can be prepared by the reaction of hydrogen fluoride with phenyl carbamic acid fluorides or their precursor phenyl isocyanates.

SUMMARY OF THE INVENTION

It has now been found that benzenamines, of the formula

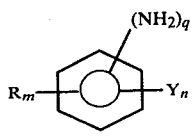

wherein
R is chlorine, fluorine, bromine, phenyl, chlorophenyl, fluorophenyl, or bromophenyl
Y is trifluoromethyl or difluoromethyl
m is 0 to 2
n is 0 to 2
q is 1 to 2
can be prepared by
(A) reacting hydrogen fluoride with a phenyl carbamic fluoride of the formula

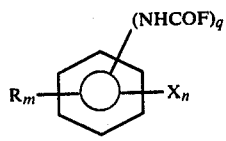

where q, m, n, and R are as defined above, and X is trichloromethyl, tribromomethyl, trifluoromethyl, dichloromethyl, dibromomethyl or difluoromethyl with the provision that when X is trichloromethyl, tribromomethyl or trifluoromethyl, Y is trifluoromethyl and when X is dichloromethyl, dibromomethyl or difluoromethyl, Y is difluoromethyl, to produce a benzenamine.hydrofluoride complex; of the formula

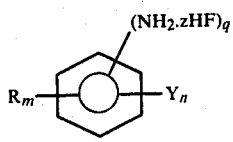

where z is about 1 to about 4 and R, Y, q, m and n are as defined above; and
(B) dissociating the benzamine.hydrofluoride complex and recovering the benzenamine.

The benzenamine.hydrofluoride resulting from the reaction of hydrogen fluoride with the phenyl carbamic fluoride in accordance with step (A), above, is a complex of variable stoichiometry. The explanation of the variable stoichiometry of these benzamine.hydrofluoride complexes is not essential to the process of this invention or the preparation or use of such complexes. However, it may be postulated that the variable stoichiometry is a result of hydrogen bonding.

The amine.HF complex can be dissociated by heating for example, to temperatures above 100° Celsius. However, at such temperatures the dissociation may be accompanied by undesireable reactions such as polymerization. In a preferred manner, the benzenamine.hydrofluoride complex can be readily dissociated by conventional methods such as neutralization with caustic or the like, and the benzenamine recovered from the reaction mixture by conventional physical separation processes such as distillation or the like. The neutralization of amine.hydrofluorides with KOH, NaOH or the like is disclosed by Berliner at al., Journal of Physical Chemistry, Vol. 32, 1142–1162, (1928).

Generally for the reaction of hydrogen fluoride with the phenyl carbamic fluoride, a temperature in the range of about −10° to about 150° Celsius and preferably about 20° to about 100° Celsius is employed. The reaction may be run neat or in the presence of a carrier medium, such as methylene chloride. The reaction proceeds smoothly, without the need for a catalyst. However, if desired, a catalyst, such as a Lewis acid catalyst may be employed.

The reaction of the phenyl carbamic acid fluoride with hydrogen fluoride is carried out in the presence of a stoichiometric excess of hydrogen fluoride to result in the formation of the benzenamine.hydrofluoride and carbonyl fluoride as a by-product. The amount of hydrogen fluoride provided to the reaction should be at least slightly in excess of the amount required for the formation of the benzenamine.hydrofluoride. Preferably the amount of hydrogen fluoride will be sufficient to provide a molar ratio of hydrogen fluoride:phenyl carbamic fluoride of between 4:1 and 30:1 or greater. It is preferred to carry out the reaction in the liquid phase either in a sealed reactor, that is, an autoclave, or at atmospheric pressure, using a cooling condenser.

The phenyl carbamic fluoride reactant may be conveniently prepared by reaction of the corresponding phenyl isocyanate with hydrogen fluoride. The reaction may be carried out in the liquid or vapor phase. In the liquid phase the reaction may be carried out at atmospheric pressure, with the temperature being maintained at below the boiling point of hydrogen fluoride, or at higher pressures and temperatures under autogenous conditions. It is preferred to carry out the reaction neat. However, if desired, a carrier medium such as methylene chloride may be employed. Typically, for a liquid phase reaction, temperatures in the range of about 20° to about 100° Celsius are employed. In a vapor phase reaction the temperature will generally be above the boiling point of the reaction mixture with no practical upper limit. Typically, the vapor phase reaction is run at a temperature of about 250° to about 350° Celsius. It is preferred to carry out the reaction with at least slight stoichiometric excess of hydrogen fluoride present at all times. Although there is no practical upper limit to the molar ratio of hydrogen fluoride to organic reaction employed, a ratio between about 5:1 and about 25:1 is generally employed.

It has been found that when hydrogen fluoride is reacted with a 1-isocyanato-2-(trihalomethyl)benzene to prepare a 2-(trifluoromethyl)phenyl carbamic fluoride, the in situ formation of N-(trifluoromethyl)-anthraniloyl fluoride occurs during the reaction. The anthraniloyl fluoride may be isolated and recovered. However, if left under reaction conditions, a rearrangement or isomerization of the N-(trifluoromethyl) anthraniloyl fluoride takes place rapidly and the 2-(trifluoromethyl)phenyl carbamic fluoride is formed. This intemediate formation of an N-(trifluoromethyl)anthraniloyl fluoride and the isomerization thereof has only been found in reactions involving ortho-trihalomethyl-substituted phenyl isocyanates, such as 1-isocyanato-2-(trihalomethyl)benzene and ring substituted derivatives, and does not appear to occur in reactions involving meta- or para-trihalomethylsubstituted phenyl isocyanates. A detailed description of the synthesis of 2-(trifluoromethyl)phenyl carbamic fluoride by reaction of 1-isocyanato-2-(trihalomethyl)benzene with hydrogen fluoride is disclosed in the commonly assigned application of Lin et al., entitled "Method for the Preparation of 2-(Trifluoromethyl)Phenyl Carbamic Fluoride" and concurrently filed herewith.

The phenyl carbamic fluoride reactant may be employed in substantially pure form or as the crude product of the reaction of hydrogen fluoride and a phenyl isocyanate prepared as described above. Thus, in one aspect, this invention provides a process for the preparation of benzenamine which comprises reacting a phenyl isocyanate with hydrogen fluoride to form a phenyl carbamic acid fluoride and continuing the reaction of the phennyl carbamic acid fluoride with hydrogen fluoride to produce the benzenamine.

In another aspect of the present invention, it has been found surprisingly that the reaction of a phenyl carbamic fluoride with hydrogen fluoride to form the benzamine hydrofluoride, may be accelerated by the addition of water to the reaction mixture. The amount of water added to the reaction mixture is not critical and will be effective even in trace amounts. Typically, the amount of water employed will be in the range of about 0.001 to about 2.0 moles of water per mole of phenyl carbamic fluoride. Thus, in a preferred embodiment of this invention, the reaction of hydrogen fluoride with phenyl carbamic fluoride is carried out in the presence of 4 to about 30 moles of hydrogen fluoride per mole of phenyl carbamic fluoride, and in the further presence of about 0.001 to about 2.0 moles of water per mole of phenyl carbamic fluoride to form the corresponding benzamine.hydrofluoride.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1-6

Preparation of 2-(Trifluoromethyl)Benzenamine from 2-(Trifluoromethyl)Phenyl Carbamic Fluoride

Example 1

Three hundred and two parts of 2-(trifluoromethyl)phenyl carbamic fluoride was charged to a polytetrafluoroethylene reaction vessel and maintained at 0° C. while 420 parts of liquid hydrogen fluoride was added. The reaction vessel was then sealed and the temperature was increased to about 20° C. and maintained thereat, with agitation, for about 16 hours. The reaction vessel was then opened to atmospheric pressure. Anaylsis of the organic liquid reaction product by gas chromatographic techniques indicated 54.6% 2-(trifluoromethyl)benzenamine, and 45.4% of 2-(trifluoromethyl)phenyl carbamic fluoride starting material.

Example 2

2-(Trifluoromethyl)phenyl carbamic fluoride was prepared in situ by the reaction of 187 parts of 1-isocyanato-2-(trifluoromethyl)benzene and 336 parts of hydrogen fluoride added over a 15 minute period at 0° C. Eighteen parts of water was added to the 2-(trifluoromethyl)phenyl carbamic fluoride reaction product and the temperature was increased to about 60° C. The temperature was maintained thereat while hydrogen fluoride was continually refluxed and returned to the reaction mixture. After 24 hours, analysis of the liquid reaction mixture, using gas chromatographic techniques, indicated that the organic reaction product contained 99 percent 2-(trifluoromethyl)benzenamine and 1.0 percent 2-(trifluoromethyl)phenyl carbamic fluoride.

The liquid reaction product is made alkaline by addition of NaOH and distilled under reduced pressure to recover 2-(trifluoromethyl)benzenamine.

Examples 3-6

The procedure of example 2 was repeated except that conditions were varied as shown, with the results as set forth in Table I, below.

| | | | | | Organic Product Composition (%) | |
|---|---|---|---|---|---|---|
| Example | Temperature (°C.) | Pressure Conditions | HF (Parts) | H₂O (Parts) | 2-(trifluoromethyl) benzenamine | 2-(trifluoromethyl) phenyl carbamic fluoride |
| 2 | 60 | Atmospheric[1] | 336 | 18 | 99 | 1 |
| 3 | 25 | Atmospheric[1] | 355 | 18 | 63.3 | 36.7 |
| 4 | 25 | Autogenous | 338 | 18 | 54.9 | 45.1 |
| 5 | 60 | Atmospheric[1] | 355 | 0 | 49.9 | 50.1 |
| 6 | 25 | Autogenous | 394 | 0 | 22.2 | 77.1 |

[1]HF Reflux Conditions

EXAMPLE 7

Preparation of 2-(Trifluoromethyl)Benzenamine 2-(Trifluoromethyl)phenyl carbamic fluoride was prepared in situ by the reaction of 515 parts of 1-isocyanato-2-(trichloromethyl)benzene and 1015 parts of hydrogen fluoride added over a period of about 2 hours at a temperature of about 0°-4° C. The reaction mixture was then sealed in a polytetrafluoroethylene reactor heated to about 24° C. and maintained thereat, with agitation, for about 48 hours. The reactor was then opened and equipped with a cooling condenser. Thirty-nine parts of water was added and the reaction mixture was stirred at atmospheric pressure for about 48 hours. The reactor was then opened and equipped with a cooling condenser. Thirty-nine parts of water was added and the reaction mixture was stirred at atmospheric pressure for 120 hours. The reaction mixture was then swept with nitrogen to remove hydrogen fluoride, and rendered alkaline by slow addition of 305 parts of 20% aqueous sodium hydroxide, washed with methylene chloride, then distilled under reduced pressure to yield 293 parts of 2-(trifluoromethyl)benzenamine.

EXAMPLE 8

Preparation of 3-(Trifluoromethyl)Benzenamine 3-(Trifluoromethyl)phenyl carbamic fluoride was prepared in situ by the reaction of 187 parts of 1-isocyanato-3-(trifluoromethyl)benzene and 370 parts of hydrogen fluoride added over a period of about 15 minutes at about 4° C. The reaction mixture was then sealed in a polytetrafluoroethylene reaction vessel, heated to about 24° C., and maintained thereat, with agitation, for about 96 hours. The reaction vessel was then opened to atmospheric pressure and most of the hydrogen fluoride and carbonyl fluoride gases removed. The remaining organic product was analyzed by gas chromatographic techniques, using n-pentadecane as an internal standard, indicating a yield of 41 parts of 3-(trifluoromethyl)benzenamine.

EXAMPLE 9

Preparation of 4-Chloro-2-(Trifluoromethyl)Benzenamine

4-Chloro-2-(trifluoromethyl)phenyl carbamic fluoride was prepared in situ by the reaction of 221 parts of 4-chloro-2-(trifluoromethyl)-isocyanatobenzene and 380 parts of hydrogen fluoride added over a period of about 15 minutes at about 4° C. The reaction mixture was then sealed in a polytetrafluoroethylene reactor, heated to about 24° C. and maintained at about that temperature, with agitation, for about 96 hours. The reactor was then opened to atmospheric pressure and most of the hydrogen fluoride and carbonyl fluoride gases removed. Analysis of the remaining organic product by gas chromatographic techniques, using n-pentadecane as an internal standard, indicated as yield of 55 parts of 4-chloro-2-(trifluoromethyl)benzenamine.

EXAMPLE 10

Preparation of 4-Chloro-3-(Trifluoromethyl)Benzenamine

4-Chloro-3-(trifluoromethyl)phenyl carbamic fluoride was prepared in situ by the reaction of 221 parts of 4-chloro-3-(trifluoromethyl)isocyanatobenzene and 450 parts of hydrogen fluoride added over a period of 15-20 minutes at about 4° C. The reaction mixture was then sealed in a polytetrafluoroethylene reactor, heated to about 24° C. and maintained thereat, with agitation, for about 96 hours. The reactor was then opened to atmospheric pressure and most of the hydrogen fluoride and carbonyl fluoride gases removed. Analysis of the remaining organic product by gas chromatographic techniques, using n-heptadecane as an internal standard indicated a yield of 77 parts of 4-chloro-3-(trifluoromethyl)benzenamine.

EXAMPLE 11

Preparation of 4-(Trifluoromethyl)Benzenamine 4-(Trifluoromethyl)phenyl carbamic fluoride was prepared in situ by the reaction of 224 parts of 1-isocyanato-4-(trifluoromethyl)benzene and 460 parts of hydrogen fluoride added over a period of about 35 minutes at about 3° C. The reaction mixture was then sealed in a polytetrafluoroethylene reaction vessel, heated to about 24° C., and maintained thereat, with agitation, for about 112 hours. Infra-red analysis of the gaseous phase, when the reaction vessel was opened to atmospheric pressure, indicated large quantities of carbonyl fluoride present. The remaining organic product was analyzed by gas chromatographic techniques, using n-pentadecane as an internal standard, indicating a yield of 114 parts of 4-(trifluoromethyl)benzenamine.

What is claimed is:

1. A method for the preparation of benzenamine.hydrofluoride complexes of the formula

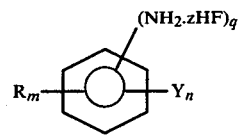

wherein R is chlorine, fluorine, bromine, phenyl, chlorophenyl, fluorophenyl, or bromophenyl; Y is trifluoromethyl or difluoromethyl; m is 0 to 2; n is 0 to 2; z is about 1 to about 4; and q is 1 to 2; which comprises reacting hydrogen fluoride with a phenyl carbamic fluoride of the formula

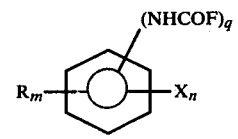

where q, m, n, and R are as defined above, and X is trichloromethyl, tribromomethyl, trifluoromethyl, dichloromethyl, dibromomethyl or difluoromethyl with the provision that when X is trichloromethyl, tribromomethyl or trifluoromethyl, Y is trifluoromethyl and when X is dichloromethyl, dibromomethyl or difluoromethyl, Y is difluoromethyl.

2. A method according to claim 1 wherein Y is —CF$_3$ and n is 1.

3. A method according to claim 2 wherein q is 1.

4. A method according to claim 3, for the preparation of benzenamine.hydrofluoride complexes of the formula

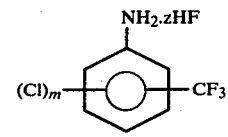

where m is 0 or 1, which comprises reacting hydrogen fluoride with a phenyl carbamic fluoride of the formula

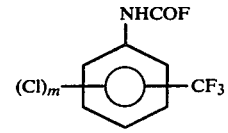

where m is as defined above.

5. A method according to claim 4 carried out at a temperature of about 20° to about 100° Celsius.

6. A method according to claim 4 wherein the molar ratio of hydrogen fluoride:phenyl carbamic fluoride is 4:1 to 30:1.

7. A method according to claim 4 wherein the phenyl carbamic fluoride is 2-(trifluoromethyl)phenyl carbamic fluoride and the benzenamine.hydrofluoride complex prepared is 2-(trifluoromethyl)benzenamine.-hydrofluoride.

8. A method according to claim 4 wherein the phenyl carbamic fluoride is 3-(trifluoromethyl)phenyl carbamic fluoride and the benzenamine.hydrofluoride is 3-(trifluoromethyl)benzenamine.hydrofluoride.

9. A method according to claim 4 wherein the phenyl carbamic fluoride is 4-(trifluoromethyl)phenyl carbamic fluoride and the benzenamine.hydrofluoride complex prepared is 4-(trifluoromethyl)benzenamine.-hydrofluoride.

10. A method according to claim 4 wherein the phenyl carbamic fluoride is 4-chloro-2-(trifluoromethyl)phenyl carbamic fluoride and the benzenamine.hydrofluoride complex prepared is 4-chloro-2-(trifluoromethyl)benzenamine.hydrofluoride.

11. A method according to claim 4 wherein the phenyl carbamic fluoride is 4-chloro-3-(trifluoromethyl)phenyl carbamic fluoride and the benzenamine.hydrofluoride complex prepared is 4-chloro-3-(trifluoromethyl)benzenamine.hydrofluoride.

12. A method according to claim 4 wherein the phenyl carbamic fluoride is prepared in situ by the reaction of hydrogen fluoride with a phenyl isocyanate of the formula

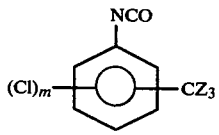

where m is as defined, and Z is halo

13. A method according to claim 12 wherein m is 0.

14. A method according to claim 6 wherein water is present in an amount of about 0.001 to about 2.0 moles per mole of phenyl carbamic fluoride.

15. A method according to claim 1 wherein the benzenamine.hydrofluoride complex is dissociated and a benzenamine of the formula

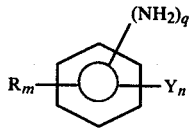

where R, Y, m, n and q are as defined, is recovered.

16. A method according to claim 15 wherein the reaction of hydrogen fluoride with a phenyl carbamic fluoride is carried out at a temperature of about −10° to about 150° Celsius.

17. A method according to claim 15 wherein the molar ratio of hydrogen fluoride:phenyl carbamic fluoride is about 4:1 to about 30:1.

18. A method according to claim 15 wherein the phenyl carbamic fluoride is 2-(trifluoromethyl)phenyl carbamic fluoride and the benzenamine prepared is 2-(trifluoromethyl)benzenamine.

19. A method according to claim 15 wherein the phenyl carbamic fluoride is 3-(trifluoromethyl)phenyl carbamic fluoride and the benzenamine prepared is 3-(trifluoromethyl)benzenamine.

20. A method according to claim 15 wherein the phenyl carbamic fluoride is 4-(trifluoromethyl)phenyl carbamic fluoride and the benzenamine prepared is 4-(trifluoromethyl)benzenamine.

21. A method according to claim 15 wherein the phenyl carbamic fluoride is 4-chloro-2-(trifluoromethyl)phenyl carbamic fluoride and the benzenamine prepared is 4-chloro-2-(trifluoromethyl)benzenamine.

22. A method according to claim 15 wherein the phenyl carbamic fluoride is 4-chloro-3-(trifluoromethyl)phenyl carbamic fluoride and the benzenamine prepared is 4-chloro-3-(trifluoromethyl)benzenamine.

23. A method according to claim 15 wherein the phenyl carbamic fluoride is of the formula

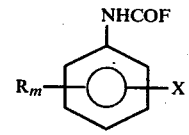

where R, m and X are as defined, and the benzenamine prepared is of the formula.

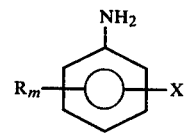

where X, R, and m are as defined.

24. A method according to claim 23 wherein the phenyl carbamic fluoride is prepared in situ by the reaction of hydrogen fluoride with a phenyl isocyanate of the formula

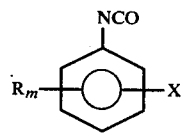

where X, R, and m are as defined.

25. A method according to claim 18 wherein the 2-(trifluoromethyl)phenyl carbamic fluoride is prepared in situ by reaction of 1-isocyanato-2-(trifuoromethyl)-benzene with hydrogen fluoride.

26. A method according to claim 19 wherein the 3-(trifluoromethyl)phenyl carbamic fluoride is prepared in situ by reation of 1-isocyanato-3-(trifluoromethyl)-benzene with hydrogen fluoride.

27. A method according to claim 20 wherein the 4-(trifluoromethyl)phenyl carbamic fluoride is prepared in situ by reaction of 1-isocyanato-4-(trifluoromethyl)-benzene with hydrogen fluoride.

28. A method according to claim 21 wherein the 4-chloro-2-(trifluoromethyl)phenyl carbamic fluoride is prepared in situ by reaction of 4-chloro-2-(trifluoromethyl)-isocyanatobenzene with hydrogen fluoride.

29. A method according to claim 22 wherein the 4-chloro-3-(trifluoromethyl)phenyl carbamic fluoride is prepared in situ by reaction of 4-chloro-3-(trifluoromethyl)-isocyanatobenzene with hydrogen fluoride.

* * * * *